United States Patent [19]

Cody

[11] Patent Number: 5,558,623

[45] Date of Patent: Sep. 24, 1996

[54] THERAPEUTIC ULTRASONIC DEVICE

[75] Inventor: G. Lee Cody, Inola, Okla.

[73] Assignee: Rich-Mar Corporation, Inola, Okla.

[21] Appl. No.: 413,086

[22] Filed: Mar. 29, 1995

[51] Int. Cl.$^6$ .................................................... A61B 17/22
[52] U.S. Cl. ........................ 601/2; 128/660.03; 128/662.03
[58] Field of Search .................. 601/2; 128/660.03, 128/660.01, 660.1, 662.03; 310/311, 324

[56] References Cited

U.S. PATENT DOCUMENTS

| | | | |
|---|---|---|---|
| 3,102,535 | 9/1963 | Dailey | 601/2 |
| 4,413,629 | 11/1983 | Durley | 128/660 |
| 4,517,985 | 5/1985 | Teslawski et al. | 128/660 |
| 4,530,362 | 7/1985 | Hetz | 128/660 |
| 4,674,517 | 6/1987 | Barnes et al. | 128/662.03 |
| 4,708,127 | 11/1987 | Abdelghani | 601/2 |
| 4,748,985 | 6/1988 | Nagasaki | 128/660 |
| 4,823,042 | 4/1989 | Coffey et al. | 310/322 |
| 4,870,972 | 10/1989 | Maerfeld et al. | 128/662.03 |
| 4,972,839 | 11/1990 | Angelsen | 128/662.06 |
| 5,123,405 | 6/1992 | McShirley et al. | 601/2 |
| 5,139,013 | 8/1992 | Bell | 601/2 |
| 5,186,176 | 2/1993 | Hiki et al. | 128/662.03 |

Primary Examiner—Marvin M. Lateef
Assistant Examiner—Brain L. Casler
Attorney, Agent, or Firm—Dougherty, Hessin, Beavers & Gilbert

[57] ABSTRACT

A therapeutic ultrasonic device which will transmit multiple ultrasonic frequencies through one ultrasonic applicator. The applicator includes a handle; two diaphragms connected to one end of the handle with each diaphragm having an applicating face directed away from the handle and a rear face directed into the handle so that the applicating faces may be independently applied to a patient during therapy; and at least two piezoelectric crystals. A piezoelectric crystal is connected to the rear face of each diaphragm for converting periodic electrical energy into ultrasonic energy and transmitting the ultrasonic energy through the diaphragm to which the crystal is connected independently of the other diaphragm. An excitation source is provided for independently applying a periodic electric field of selectable frequency across a crystal in order to select the crystal to receive the periodic electric field and to select the ultrasonic frequency transmitted through the diaphragm to which the selected crystal is connected.

11 Claims, 2 Drawing Sheets

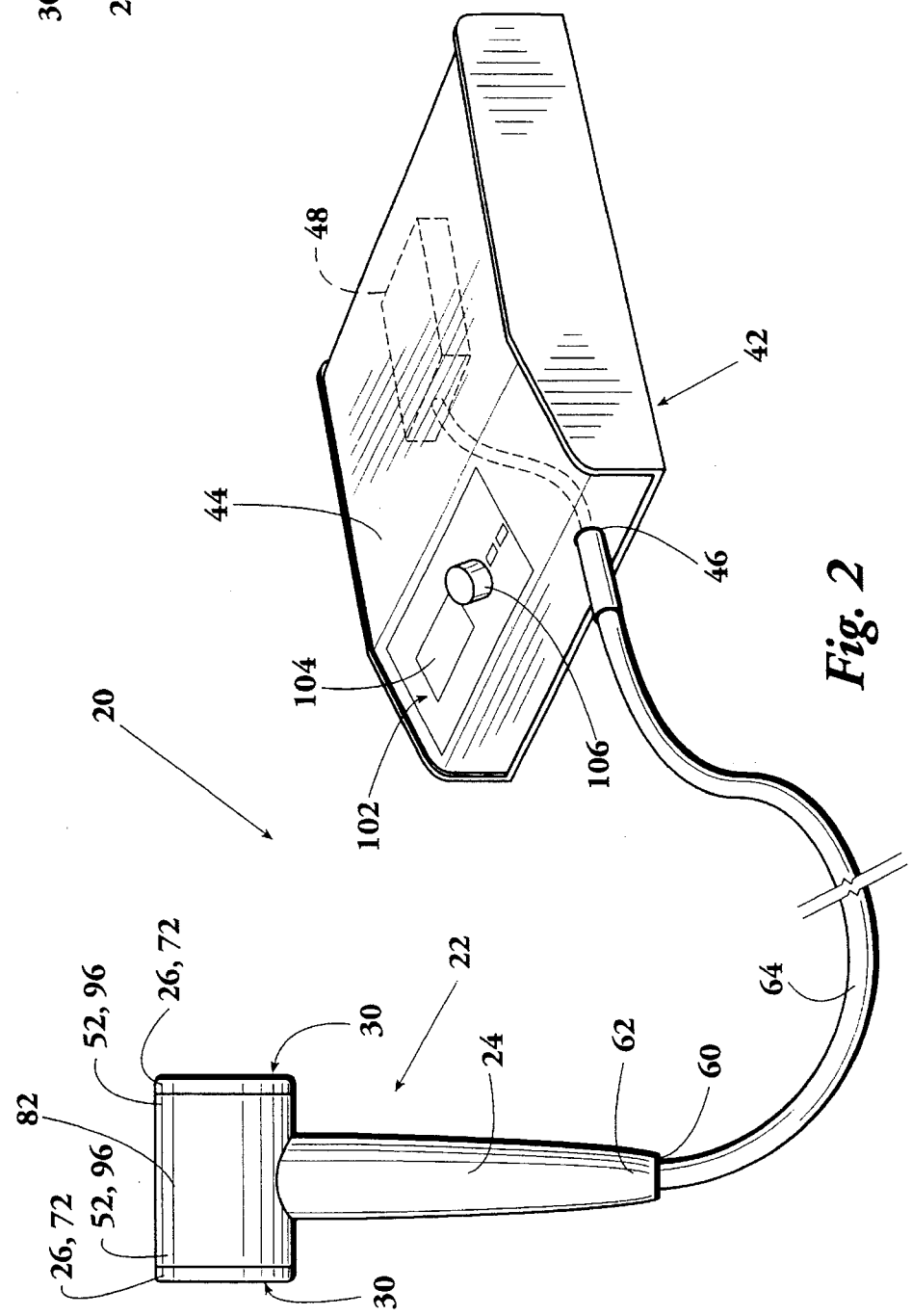

THERAPEUTIC ULTRASONIC DEVICE

BACKGROUND OF THE INVENTION

This invention relates to therapeutic ultrasonic devices and more particularly, but not by way of limitation, to ultrasonic applicators which use a piezoelectric crystal to convert electrical energy into ultrasonic energy.

Ultrasonic transducers which use a piezoelectric transducer in medical imaging and diagnostic applications are known. For example, U.S. Pat. No. 4,870,972 (Maerfeld et el.) discloses a multiple-frequency acoustic transducer for medical imaging. The Maerfeld transducer uses strips on opposite faces of a single transducer to enable each face of the transducer to be used to provide imaging at a different frequency.

U.S. Pat. No. 4,972,839 (Angelsen) discloses an ultrasonic probe for use in medical imaging which has transducers mounted on opposite sides of an acoustically isolating material. The transducers emit different ultrasonic frequencies with one of the transducers selected at any particular time and connected to an associated ultrasonic scanner.

U.S. Pat. No. 4,530,362 (Hetz) discloses an ultrasound transmitting/receiving system for sector scanning which is primarily intended for cardiac examinations. Hetz uses a single electromagnetic drive to activate transducers on opposed ends of an applicator housing. The single drive is used to nullify mechanical inertia forces which would otherwise result within the opposed ends.

U.S. Pat. No. 4,748,985 (Nagasaki) discloses two transducer elements fixed back to back with a damper medium interposed between the transducer elements for use in an endoscope for ultrasonic imaging. The transducers transmit ultrasonic waves, receive the echo and convert the echo into echo signals.

The previously discussed patents do not disclose or suggest a therapeutic ultrasonic device having a single ultrasonic applicator which may be used to apply ultrasonic therapy at multiple frequencies. Therapeutic ultrasonic applicators are used to apply ultrasonic energy directly to the body of a patient, particularly to muscle, fat, or bone, in order to stimulate healing of damaged tissue.

Prior therapeutic ultrasonic devices use applicators having only one applicator surface or diaphragm. Typically, such devices are operable at at least two ultrasonic frequencies and either use two applicators having separate cables, handles, etc., to interchangeably connect the applicators to a control console; or have multiple applicators, housings, cables, etc. connected directly to the control console. The sonic transducer described in U.S. Pat. No. 4,823,042 (Coffey et al.), which is assigned to the assignee of the present invention, and which is incorporated herein by reference thereto, is typical of such devices.

There are problems created by the unavailability of a therapeutic ultrasonic device having a single ultrasonic applicator which will operate at multiple ultrasonic frequencies. For example, the use of multiple independent applicators connected to one control console creates an expensive redundancy of componentry, a higher probability of failure of one of the applicators, and requires the therapist to stop therapy to change the size or frequency of the applicator. If the applicators must be physically changed, i. e., if there is only one connection to the control console and multiple applicators which may be connected thereto, the disconnectable connection creates a point of entry for moisture and other contaminants, the likelihood of a faulty connection, and a likelihood that the control console will not be properly tuned (set to the proper excitation frequency) for the applicator connected to the console, which impairs the therapeutic effects of the applicator. The oscillator or other periodic energy source must be set at a frequency which matches the resonant frequency of the piezoelectric transducer for the applicator to function properly.

Therefore, there is a need for a therapeutic ultrasonic device having a single ultrasonic applicator which will operate at multiple ultrasonic frequencies.

SUMMARY OF THE INVENTION

It is contemplated that the present invention overcomes the foregoing deficiencies and meets the above-described needs. In accomplishing this, the present invention provides a novel and improved therapeutic ultrasonic device which will transmit multiple ultrasonic frequencies through one ultrasonic applicator.

The invention comprises a handle; at least two diaphragms located at one end of the handle, each diaphragm having an applicating face directed away from the handle and a rear face directed into or toward the handle so that the applicating faces may be independently applied to a patient during therapy; and at least two piezoelectric crystals, a crystal being connected to the rear face of each diaphragm for converting periodic electrical energy to ultrasonic energy and transmitting the ultrasonic energy through the diaphragm to which the crystal is connected independently of the other diaphragm.

The device also includes excitation means for independently applying a periodic electric field across each crystal. The excitation means applies a periodic electrical field of a selectable frequency across each crystal in order to select the ultrasonic frequency transmitted through the diaphragm to which the crystal is connected. The preferred excitation means includes a control console and the crystals are connected to the control console through one connection on the console. Preferably, the diaphragms and crystals are hardwired to a source of periodic electrical energy inside the control console in such a manner that the handle and diaphragms may not be disconnected from the control console without accessing the inside of the control console.

BRIEF DESCRIPTION OF THE DRAWINGS

The present invention will be better understood by reference to the example of the following drawings:

FIG. 2 is a perspective view of an embodiment of the ultrasonic device of the present invention; and FIG. 3 is a side elevational view of another embodiment of an ultrasonic applicator of the present invention.

DETAILED DESCRIPTION OF THE PREFERRED EMBODIMENT

Figure 1:
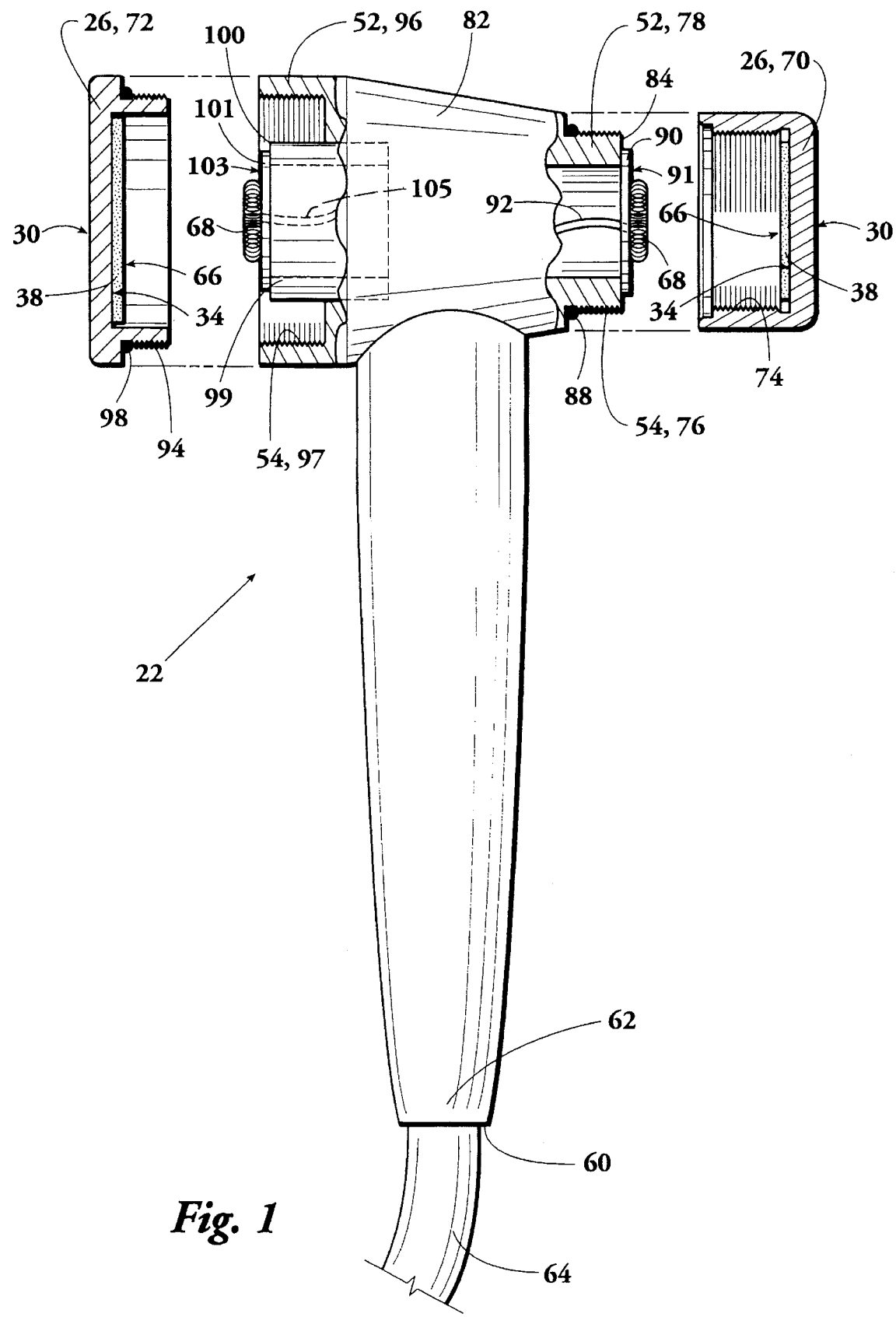
FIG. 1 is a partially sectioned side elevational view of an ultrasonic applicator of the present invention.

Preferred embodiments of the invention will now be described with reference to the drawings. Like reference characters refer to like or corresponding parts throughout the drawings and description.

FIGS. 1–3 present embodiments of the therapeutic ultrasonic device, generally designated 20, of the present invention. Referring to the example of FIG. 1, the device 20 includes an ultrasonic applicator 22 which comprises a handle 24; at least two diaphragms 26, each diaphragm having an applicating face 30 directed away from the handle 24 and a rear face 34 directed into the handle 24 so that the applicating faces 30 may be independently applied to a patient during therapy; and at least two piezoelectric crystals 38, a crystal 38 being connected to the rear face 34 of each diaphragm 26 for converting periodic electrical energy to ultrasonic energy and transmitting the ultrasonic energy through the diaphragm 26 to which the crystal 38 is connected independently of the other diaphragm.

The preferred device 20 includes excitation means 42 (FIG. 2) for independently applying a periodic electric field across each crystal. Preferably, the excitation means 42 applies a periodic electric field of selectable frequency across each crystal 38 in order to select the ultrasonic frequency transmitted through the diaphragm 26 to which the crystal 38 is connected. More preferably, the excitation means 42 includes a control console 44 and the crystals 38 are connected to the control console through one connection 46 on the console 44. In an even more preferred embodiment, referring to the example of FIG. 1, the diaphragms 26 and crystals 38 are hard-wired to a source 48 of periodic electrical energy (which may be an oscillator, AC generator, or other device which will produce an alternating electric field) inside the control console 44 in such a matter that the handle 24 and diaphragms 26 may not be disconnected from the control console 44 without accessing the inside of the control console 44.

Referring to the example of FIG. 1, the device 20 will now be described in greater detail. The preferred handle 24 is hollow and has two opposite facing connectors 52 at one end of the handle. The preferred connectors 52 are rigidly, nonmovably, and integrally formed with the handle 24. The connectors 52 have threads 54 which threadably engage with the diaphragms 26.

A cable entry 60 is provided at the second end 62 of the handle 24. A cable 64 extends from the control console 44 through the cable entry 60 and carries electrical wiring from the console to electrodes 68 in contact with the piezoelectric crystals 38, as would be known to one skilled in the art in view of the disclosure contained herein. The piezoelectric crystals 38 are preferably connected to the rear face 34 of the diaphragms 26 by chemical bonding. In the prototype applicator 22, one electrode 68 makes electrical contact with the rear surface 66 of each crystal 38. The crystal 38 is bonded to the diaphragm's rear face 34 in such a manner that electrical contact is made between the diaphragm's rear face 34 and the crystal 38 in order to complete the electrical circuit from the electrodes 68 to electrical ground.

The cable entry 60 is sealed to prevent entry of moisture and other foreign matter into the hollow handle 34. Preferably, the cable 64 may only be disconnected from the handle 34 by breaking the connections of the wiring to the electrodes 68 in order to prevent unauthorized technicians from disconnecting the applicator 22 from the control console 44. The exterior surface of the prototype handle 24 is provided with a vinyl coating, such as MARLUX®, to acoustically isolate the therapist from the ultrasonic vibrations generated by the applicator 22.

The cable 64 extends from the handle 24 to the control console 44. The cable 64 enters the control console 44 through connection 46 and is preferably disconnectably connected to the source of periodic electrical energy 48 within the control console 44. By hard-wired is meant that there are no disconnectable connections in the cable 64 between the applicator 22 and the source of periodic electrical energy 48. Since the cable is hard-wired to the electrodes 68, the only disconnectable connection is at the source 48. Therefore, the control console must be opened to disconnect the applicator 22 from the control console 44. The preferred control console 44 is designed such that it is difficult for one other than a trained technician to open the control console 44. This eliminates the problems created by an operator connecting the wrong applicator to the control console 44 and the inherent moisture entry and faulty connection problems created by disconnectable connections.

The applicating faces 30 of the diaphragms 26 may have different surface areas (FIG. 1) or have substantially equal surface areas (FIGS. 2 and 3). In the prototype applicator 22, the applicating faces 30 face in diametrically opposed directions and are separated by approximately 1.75 inches. More than two connectors 52 and diaphragms 26 may be provided if desirable.

The preferred surface areas of the applicating face 30 of diaphragm 26 are one square centimeter, two square centimeters, five square centimeters, and ten square centimeters. In the embodiment of FIG. 1, having different sizes of applicating faces 30, the preferred sizes are two square centimeters for the smaller diaphragm 70 and five square centimeters for the larger diaphragm 72.

Referring to the example of FIG. 1, in the prototype applicator 22, the smaller diaphragm 70 has internal threads 74 extending from the rear face 34 of the diaphragm 70 which engage external threads 76 on the smaller connector 78. The smaller connector 78 has an external end 84 which extends from the support housing 82 and is connected to support housing 82. Support housing 82 is connected to handle 24.

The preferred smaller connector 78 and support housing 82 are hollow and made of an electrically conductive material, the exterior of which is coated with a vinyl coating, as previously discussed. The threads 74, 76 are not coated with the vinyl coating so that the diaphragm 26, 70, connector 78, support housing 82, and handle 24 provide an electrical ground path for electrical energy passing through piezoelectric crystal 34 from electrode 68.

An isolating plate 90 is used to close the external end 84 of the smaller connector 78. The isolating plate 90 is made of a material which electrically isolates the electrode 68 from the electrically conductive smaller connector 78. In the prototype applicator 22, the end surface 91 of the isolating plate 90 is at least partially coated with copper and the electrode 68 is mounted on the copper coating. A conductor 92 extends from cable 64 through the isolating plate 90 and is electrically connected to the copper coating to ensure good electrical contact between electrode 68 and the source of periodic energy 48.

The preferred isolating plate 90 is made of fiberglass, such as is used in circuit boards. The preferred electrode 68 is a coiled spring electrode which is formed into an annular shape in order to assure good electrical contact between the electrode 68 and the rear surface 66 of crystal 38. When the smaller diaphragm 70 is fully threaded onto the smaller connector 78, the electrode 68 contacts the rear surface 66 of crystal 34 and applies periodic electrical energy to the crystal 34. The electrical energy passes through the crystal 34 to the body of the diaphragm 26, 70, smaller connector 78, support housing 82, handle 24, and cable 64 to electrical ground. A seal, such as an O-ring 88, is mounted on the smaller connector 78 adjacent the support housing 82 in such a manner that the O-ring 88 seals the connection between the smaller diaphragm 70 and support housing 82 when the smaller diaphragm 70 is threadably engaged with the connector 78. The O-ring 88 prevents the entry of moisture and other foreign matter into the applicator 22.

The larger diaphragm 72 has external threads 94 which extend from the rear face 34 of the diaphragm 72. The external threads 94 engage internal threads 97 in the larger connector 96. A seal, such as O-ring 98, is provided on the external threads 94 adjacent the rear face 34 of the larger diaphragm 72 to seal the applicator 22 against the entry of moisture and other foreign matter. A hollow housing extension 99 is connected to the support housing 82 and extends from the handle 24 into the larger connector 96. The housing extension 99 has an external end 100 extending away from the support housing 82 and handle 24. The larger connector 96 and diaphragm 72 are made of an electrically conductive material. The exterior of the larger connector 96, support housing 82, and handle 24 are coated with a vinyl coating, as previously discussed. The threads 94, 97 are not coated with the vinyl coating so that the diaphragm 72, connector 96, support housing 82 and handle 24 provide an electrical ground path for electrical energy passing through piezoelectric crystal 34 from electrode 68.

An isolating plate 101 is used to close the external end 100 of housing extension 99. The isolating plate 101 is made of a material which electrically isolates the electrode 68 from the electrically conductive housing extension 99. In the prototype applicator 22, the end surface 103 of the isolating plate 101 is at least partially coated with copper and the electrode 68 is mounted on the copper coating. A conductor 105 extends from cable 64 through the isolating plate 101 and is electrically connected to the copper coating to ensure good electrical contact between electrode 68 and the source of periodic energy 48.

The preferred isolating plate 101 is made of fiberglass, such as is used in circuit boards. The preferred electrode 68 is a coiled spring electrode placed in an annular shape in order to provide good electrical contact with the crystal 38. When the larger diaphragm 72 is fully threaded into the larger connector 96, the electrode 68 contacts the rear surface 66 of crystal 34 and applies periodic electrical energy to the crystal 34. The electrical energy passes through the crystal 34 to the body of the diaphragm 26, 72, larger connector 96, support housing 82, handle 24, and cable 64 to electrical ground.

Referring to the example of FIG. 3, in the embodiment having two smaller diaphragms 70 and connectors 78, the diaphragms 70 and connectors 52, 78 are constructed identically to the smaller diaphragms 70 and connectors 78 previously described. Similarly, referring to the example of FIG. 2, in the embodiment having two larger diaphragms 72 and connectors 52, 96, the diaphragms and connectors 52, 96 are identical to the larger diaphragms 72 and connectors 96 described previously.

In the prototype applicators, the piezoelectric crystals 38 have a thickness which is selected to provide a basic resonant frequency or fundamental frequency, of one megahertz. It is contemplated that the preferred control console 44 will be designed such that each applicating face 30 on applicator 22 may be operated at at least two frequencies, the preferred two frequencies being 1 megahertz and 3 megahertz. The crystal will operate efficiently at any frequency that is a multiple of its basic resonant frequency. Since it is contemplated that the preferred applicators will have a basic resonant frequency of one megahertz, the crystals 38 and applicators may therefore be efficiently operated at 2 megahertz, 3 megahertz, etc.

The control console 44 and oscillator should be selected to properly match with the resonant frequencies of the crystal 38. The preferred console 44 includes selection means 102, such as a graphic screen 104 and cursor dial 106, for selecting and adjusting the desired operational functions of the applicator, such as frequency, intensity, which diaphragm 26 is operational, the length of time the selected diaphragm 26 is operational, etc., as would be known to one skilled in the art in view of the disclosure contained herein.

While presently preferred embodiments of the invention have been described herein for the purpose of disclosure, numerous changes in the construction and arrangement of parts and the performance of steps will suggest themselves to those skilled in the art in view of the disclosure contained herein, which changes are encompassed within the spirit of this invention, as defined by the following claims.

What is claimed is:

1. A therapeutic ultrasonic device having an ultrasonic applicator, the applicator comprising:

a handle;

at least two diaphragms located at one end of the handle, each diaphragm having an applicating face directed away from the handle and a rear face directed into the handle so that the applicating faces may be independently applied to a patient during therapy; and at least two piezoelectric crystals, at least one of the crystals being connected to the rear face of one of the diaphragms and at least one of the other crystals being connected to the rear face of the other diaphragm for converting periodic electrical energy to ultrasonic energy and transmitting the ultrasonic energy through the diaphragm to which the crystal is connected independently of the other diaphragm.

2. Device of claim 1 comprising:

excitation means for independently applying a periodic electric field across each crystal.

3. Device of claim 2:

wherein the excitation means applies a periodic electric field of selectable frequency across each crystal in order to select the ultrasonic frequency transmitted through the diaphragm to which the crystal is connected.

4. Device of claim 3 in which the excitation means comprises:

a control console; and wherein the diaphragms and crystals are connected to the control console through one connection on the control console.

5. Device of claim 4:

wherein the diaphragms and crystals are hard-wired to a source of periodic electrical energy inside the control console in such a manner that the handle and diaphragms may not be disconnected from the control console without accessing the inside of the control console.

6. Device of claim 1:

wherein the applicating faces of the diaphragms have different surface areas.

7. Device of claim 1:

wherein the applicating faces of the diaphragms have substantially equal surface areas.

8. A therapeutic ultrasonic device which will transmit multiple ultrasonic frequencies through one ultrasonic applicator, the applicator comprising:

a handle;

two diaphragms connected to one end of the handle, each diaphragm having an applicating face directed away from the handle and a rear face directed into the handle so that the applicating faces may be independently applied to a patient during therapy; and at least two piezoelectric crystals, at least one of the crystals being connected to the rear face of one of the diaphragms and at least one of the other crystals being connected to the rear face of the other diaphragm for converting periodic electrical energy into ultrasonic energy and transmitting the ultrasonic energy through the diaphragm to which the crystal is connected independently of the other diaphragm.

9. Device of claim 8, comprising:

excitation means for selectably and independently applying a periodic electric field of selectable frequency across a crystal in order to select the crystal to receive the periodic electric field and to select the ultrasonic frequency transmitted through the diaphragm to which the selected crystal is connected.

10. Device of claim 9 in which the excitation means comprises:

a control console; and wherein the crystals are connected to the control console through one connection on the control console.

11. Device of claim 10:

wherein the diaphragms and crystals are hard-wired to a source of periodic electrical energy inside the control console in such a manner that the handle or diaphragms may not be disconnected from the control console without accessing the inside of the control console.

* * * * *